US010426840B2

United States Patent
Martins

(10) Patent No.: US 10,426,840 B2
(45) Date of Patent: Oct. 1, 2019

(54) OIL SUSPENSION OF METRONIDAZOLE

(71) Applicant: VIRBAC, Carros (FR)

(72) Inventor: Fanny Martins, Cagnes sur Mer (FR)

(73) Assignee: VIRBAC, Carros (FR)

(*) Notice: Subject to any disclaimer, the term of this patent is extended or adjusted under 35 U.S.C. 154(b) by 0 days.

(21) Appl. No.: 16/030,652

(22) Filed: Jul. 9, 2018

(65) Prior Publication Data
US 2019/0008967 A1 Jan. 10, 2019

Related U.S. Application Data

(62) Division of application No. 14/655,969, filed as application No. PCT/IB2013/061140 on Dec. 19, 2013, now abandoned.

(30) Foreign Application Priority Data

Dec. 27, 2012 (FR) ..................... 12 62823

(51) Int. Cl.
| | | |
|---|---|---|
| A61K 47/14 | (2017.01) | |
| A61K 9/14 | (2006.01) | |
| A61K 9/00 | (2006.01) | |
| A61K 9/10 | (2006.01) | |
| A61K 31/4164 | (2006.01) | |

(52) U.S. Cl.
CPC ............ *A61K 47/14* (2013.01); *A61K 9/0053* (2013.01); *A61K 9/10* (2013.01); *A61K 9/14* (2013.01); *A61K 31/4164* (2013.01)

(58) Field of Classification Search
None
See application file for complete search history.

(56) References Cited

U.S. PATENT DOCUMENTS

| | | | | |
|---|---|---|---|---|
| 5,156,842 A | * | 10/1992 | Mulligan | ............. A61K 9/0095 |
| | | | | 424/116 |
| 2003/0149090 A1 | * | 8/2003 | Gehlsen | ................ A61K 31/00 |
| | | | | 514/400 |
| 2009/0215721 A1 | * | 8/2009 | Buchman | .................. A23L 2/38 |
| | | | | 514/54 |

OTHER PUBLICATIONS

Wedgewood Pharmacy: "Metronidazole: Oral Oil Suspension", Internet Archive: Wayback Machine, Dec. 31, 2011, pp. 1-2, XP055071326, Retrieved from the Internet (Year: 2011).*
Nayak et al., Metronidazole Relieves Symptoms in Irritable Bowel Syndrome: The Confusion With So-Called 'Chronic Amebiases,' Indian Journal of Gastroenterology, (1997), 16(4), pp. 137-13 (Year: 1997).*

* cited by examiner

*Primary Examiner* — Abigail Vanhorn
*Assistant Examiner* — Sarah J Chickos
(74) *Attorney, Agent, or Firm* — Christensen O'Connor Johnson Kindness PLLC

(57) ABSTRACT

Disclosed is a palatable oral veterinary pharmaceutical composition consisting of an oil suspension of metronidazole and comprising metronidazole in an edible animal, vegetable or mineral oil and the use thereof for treating diarrhea in animals, in particular giardiasis or inflammatory diseases of the digestive tract.

18 Claims, No Drawings

OIL SUSPENSION OF METRONIDAZOLE

The present invention relates to the development of a veterinary pharmaceutical composition based on metronidazole which exhibits a good appetency for animals and to its use in the treatment of diarrhea in animals, in particular giardiasis, or also inflammatory diseases of the digestive tract.

Giardiasis (also known as lambliasis) is an intestinal infection caused by the parasite *Giardia intestinalis* or *Giardia duodenalis* (formally *Giardia lamblia*), which is a flagellated protozoan. *Giardia intestinalis* normally takes up residence in lakes, water courses or ponds contaminated by human and/or animal feces. The vegetative form (or trophozoite) lives in the duodenum and measures 15 μm. The cyst form occurs in the colon and measures approximately 10 μm; this is the infecting form which lives in the colon and which occurs in the feces. This parasite is very resistant (it survives for 2 months at 8° C.); the normal sterilization of drinking water is not sufficient to remove it; on the other hand, boiling and freezing destroy them.

Some studies describe a prevalence of 10% and 15% in cats and dogs respectively. Infections are often asymptomatic but acute and persistent or intermittent chronic diarrhea of mucoid type may develop. This is a disease which is especially frequent in communities of cats, where the transmission takes place directly. It is essentially the young animals which are affected.

*Giardia* diseases are routinely demonstrated by the direct examination of fresh feces in a saline solution and after staining, for the demonstration of trophozoites, or by sample concentration and then centrifuging, for the demonstration of cysts. Diagnosis is not always easy due to the intermittent excretion of the trophozoites and cysts. Various antigen tests are also marketed.

The recommended treatments are in particular:
the administration of fenbendazole at a dose of 50 mg/kg of body weight per day for 5 days; this is the treatment most suitable for kittens and puppies;
the administration of metronidazole at a dose of 25 mg/kg of body weight twice daily for 5 days.

Furthermore, it is advisable to decontaminate the environment of the animal using ammonia-based solutions and to bath the animal in order to remove the cysts which would be present on the fur.

Metronidazole is an antibiotic and an antiparasitic belonging to the nitroimidazoles.

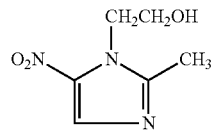

Chemical Structure of Metronidazole

It inhibits the synthesis of nucleic acids and is used in the treatment of infections related to anaerobic bacteria and also to protozoans. It is effective against, inter alia: *Giardia duodenalis, Entamoeba histolytica, Trichomonas vaginalis*, bacteria of the *Clostridium* genus or also *Helicobacter pylori*.

Metronidazole can be administered in the oral, intravenous or topical form. In the oral form, it is absorbed and passes into the bloodstream, where it has a half-life of 6 to 8 hours.

Metronidazole is normally prescribed by veterinarians to treat diarrhea in dogs, in particular giardiasis, and also chronic inflammatory diseases of the intestines in cats.

Nevertheless, there does not currently exist a veterinary pharmaceutical composition and the administration of metronidazole to animals takes place with medicaments intended for man, usually in the form of tablets; this presents several problems:
the form of the human medicaments generally has to be modified in order to render it compatible with the administration to an animal (dissolution of a tablet, for example);
their dose does not correspond to that necessary for the animal and thus has to be adjusted. In addition to being a constraint for the carer of the animal, this "redosing" represent a risk of error, indeed even of undesirable overdosing with metronidazole, the commonest symptoms of which are vomiting, complete loss of appetite, problems of coordination, fits of giddiness, and the like;
finally, metronidazole is an extremely bitter active principle; it is a product with a persistent metallic aftertaste which results in lack of appetite and in aversion; it is consequently difficult to make animals accept medicament comprising metronidazole and to obtain sufficient observance.

It is in order to overcome these inconveniences that the applicant company has attempted to develop an oral veterinary pharmaceutical composition comprising metronidazole which exists in the liquid form as this is a pharmaceutical form which is economical to produce and very easy to dose. It has thus succeeded in preparing an oily metronidazole suspension which, in addition to being stable and to exhibiting a form which facilitates the dosing and the oral administration to animals, proves to have an excellent appetency.

There are known, from the state of the art, specific pharmaceutical dosage formulations for masking the taste of active principles which require it; for example, the international application WO 2004/058137 provides such a formulation in which 15% to 30% of active principle are mixed with 60% to 80% of a glycerol ester or of a fatty acid and of a surfactant; spray cooling of the mixture is subsequently carried out in order to obtain solid particles with a particle size of less than 350 μm.

However, while carrying out its studies on developing a liquid medicament, the applicant company found that mixing of the active principle with the glycerol ester or the fatty acid was not essential in order for the medicament to be accepted by the animals and that an oily suspension of metronidazole particles having a specific size was very well accepted by animals despite the absence of coating of said particles. The fact of avoiding the coating presents obvious advantages with respect to the state of the art, among which may be mentioned, for example, a reduction in the number of ingredients and of stages necessary for the preparation of the coating, which results in a simplification in the manufacture and in a saving in terms of production costs.

The present invention thus relates to an oral veterinary pharmaceutical composition consisting of an oily metronidazole suspension comprising:
between 5% and 30% by weight/volume of metronidazole; and
between 70% and 95% by weight/volume of at least one oily vehicle;
characterized in that the metronidazole is provided in the form of particles, 90% of which have an equivalent diameter strictly greater than 6 μm; preferably, 90% of the metronidazole particles have an equivalent diameter strictly greater than 6 µm and less than or equal to 300 µm; more preferably, 90% of the metronidazole particles have an equivalent diameter of strictly between 50 and 250 µm; more preferably, 90% of the metronidazole particles have an equivalent diameter of strictly between 90 and 250 µm, more preferably 90% of the metronidazole particles have an equivalent diameter of strictly between 125 and 250 µm or between 90 and 200 µm, and more preferably still 90% of the metronidazole particles have an equivalent diameter of strictly between 125 and 200 µm; the equivalent diameter is measured by laser particle sizing, for example using a device of the Laser Malvern Mastersizer 2000 type. These measurements make it possible to obtain D50 (maximum size of at least 50% of the particles) values and also D90 (maximum size of at least 90% of the particles) values.

The expression "equivalent diameter" or "diameter" denotes, in the context of the present invention, the equivalent sphere diameter, that is to say the mean diameter of the particle, which is regarded, by approximation, as a perfect sphere. Alternatively, the particles are passed through sieves, for example Retsch sieves, for example with a diameter of 20 cm. The sieving has the effect of only allowing particles with a size of less than the value of the sieve to pass through the meshing: for example, a 180 µm sieve will make it possible to obtain a composition, 100% of the particles of which have a particulate size of less 180 µm in at least one of their dimensions. The value of the meshing of the sieve is comparable, in the context of the present invention, to a D90 value within the meaning of the laser particle sizing.

The applicant company has demonstrated experimentally, as exhibited in the examples which follow, that the use of metronidazole in the form of particles having a specific range of diameters presents a very good appetency; this is because the animals accept receiving the treatment without refusing when it is administered to them directly in the mouth and spontaneously take food supplemented with the oily suspension or consume it completely, in comparison with a nonsupplemented food; this good acceptance is observed only when the metronidazole is suspended in an oily vehicle, in particular oil; indeed, the applicant company has been able to observe, during tests which it carried out, that the acceptance of metronidazole in the same form in aqueous suspension is not satisfactory.

Surprisingly and although this range covers quite high particle diameters, the applicant company has been able to confirm that the physical stability of the oily metronidazole suspensions according to the invention is excellent and in accordance with regulatory requirements.

Preferably, the metronidazole content is between 8% and 17% by weight/volume.

The synthesis of metronidazole has been known since the 1960s and is widely described in the state of the art ("Synthesis and trichomonacidal action of metronidazole and its 4-nitroisomer", Pershin et al., Meditsinskaya Promyshlennost (1964), 18(10), 12-16, GB 939 681, FR 1379915 or U.S. Pat. No. 3,178,446); this active principle can also be ordered from suppliers of active principles.

The oily vehicle which is usable according to the invention is a vehicle predominantly comprising oil, that is to say an edible animal, vegetable or mineral oil; it can be solid or liquid at ambient temperature; however, preference is given to oils which are liquid from 15° C. Use may be made, among vegetable oils, of soybean oil, coconut oil, palm oil, sunflower oil or their mixture; these oils can also be modified or derived, as in Miglyol® products (SASOL), which are esters derived from fatty acid, which is found, for example, in palm oil or coconut oil, coupled with glycerol or propylene glycol; the oil of animal origin can be chosen from fish oils or cod liver oil and the mineral oil can be paraffin oil. The oil which is particularly suitable for the implementation of the present invention is Miglyol, in particular Miglyol 812N.

The oral veterinary pharmaceutical composition according to the invention can additionally comprise:
 between 0.1% and 5% by weight/volume of viscosifying agent chosen, for example, from aluminum mono-, di- or tristearate, hydrophilic colloidal silica (Aerosil 200) or hydrogenated castor oil (Cutina HR or Thixcin R); and/or
 between 0.1% and 5% by weight/volume of at least one surface-active principle chosen, for example, from: stearic acid, polysorbate 80 (Tween 80) or any other nonionic surfactant.

The oral veterinary pharmaceutical composition according to the invention can also comprise:
 between 0.1% and 15% by weight/volume of a natural or artificial flavoring, preferably between 1% and 5% by weight/volume for natural flavoring and between 1% and 3% by weight/volume for artificial favoring; mention may be made of chicken liver powder, baker's yeast, sucralose, chicken flavoring, anchovy flavoring, sponge cake flavoring, brewer's yeast, meat meals, fish meals, powders formed from cheeses or milk derivatives, and their mixture; this flavoring can optionally be mixed with a taste enhancer, such as monosodium glutamate;
 between 0.005% and 2% by weight/volume of at least one antioxidant, preferably between 0.01% and 0.5% by weight/volume, chosen from butylated hydroxyanisole (BHA), butylated hydroxytoluene (BHT), propyl gallate, ascorbyl palmitate, α-tocopherol and their mixtures.

The composition according to the invention can additionally comprise food dyes conventionally formulated according to the general knowledge of a person skilled in the art.

According to another of its subject matters, the present invention relates to the use of the compositions in the treatment of inflammatory diseases of the intestines of domestic animals.

In the context of the present invention, domestic animals or pets comprise dogs, cats, rodents (hamsters, mice, rats or ferrets, for example) and horses; the compositions according to the invention are particularly suitable for the treatment of diarrhea and giardiasis; they are also particularly suitable for the treatment of inflammatory diseases of the digestive tract, such as inflammatory bowel disease (IBD) in dogs or chronic inflammation of the intestines in cats. In the context of this type of treatment, the recommended doses are such that they represent a contribution of metronidazole of between 10 and 15 mg/kg of body weight administered twice daily; this type of treatment generally lasts for 3 to 10 consecutive days, in particular for 5 consecutive days.

The present invention also relates to the use of the oily metronidazole suspensions in the treatment of diarrhea, in particular diarrhea of parasitic or viral origin, in particular giardiasis, in domestic animals, in particular in dogs. For the treatment of pathologies of this type, the recommended doses are such that they represent a contribution of metronidazole of the order 25 mg/kg of body weight administered twice daily; generally administered for 3 to 10 consecutive days, in particular for 5 consecutive days.

The compositions are of particular use in the treatment of young animals; the term "young animal" is understood to mean an animal which has not reached adult age and size; this age varies according to the animal breeds under consideration; in the context of the present invention, it will be considered that young animal denotes an animal which is not adult and which is not capable of reproducing; usually, animals of less than 8 months, preferably of less than 6 months, are concerned.

Thus, depending on the animals to be treated and on the nature and the severity of their disorder, the compositions according to the invention must provide a contribution of metronidazole of between 10 and 50 mg/kg of body weight, preferably between 20 and 30 mg/kg of body weight, administered twice daily.

The concentrations and the volumes of the compositions according to the invention are adjusted according to the therapeutic requirements (disease) and the weight of the animal to be treated; for reasons of convenience of administration, preference will be given, however, to compositions having a volume of between 0.5 and 10 ml, preferably between 1 and 6 ml, more preferably of less than 3 ml.

According to a specific embodiment, the compositions according to the invention are packaged in a device which makes possible the dosing; in particular in a bottle, for example, having a volume of between 10 and 100 ml, with a measuring container which makes possible the dosing, such as a ladle, a pipette or a graduated syringe; the syringe exhibits the advantage of making possible the administration of the medicament directly into the mouth of the animal.

The compositions according to the invention exhibit a marked advantage because of their ease of use: the liquid form makes possible easy and rapid dosing; they can subsequently be administered directly into the mouth of the animal, for example using a pipette, deposited alone in the bowl of the animal or also added to the food intake of the animal.

The process for the preparation of the compositions according to the invention can be adjusted according to the viscosifying agent used.

For example, the specific case of the aluminum monostearate/stearic acid mixture (or of the aluminum distearate/stearic acid mixture) requires a process employing a phase of heating under strong shearing and then a phase of cooling under very low stirring in order not to break the gel. According to a specific example which a person skilled in the art will know how to adjust according to the ingredients used, the process can use a rotor/stator and a jacketed vessel and can comprise the following stages:

mixing, with stirring and heating, the oil (for example, Miglyol) and the antioxidant (for example, BHT);
adding stearic acid when the temperature reaches approximately 50° C. (this temperature can vary according to the scale on which the process is carried out);
adding aluminum mono-, di- or tristearate when the temperature reaches approximately 90° C.;
maintaining strong shearing at approximately 120° C. for 20 minutes;
cooling under very low stirring;
adding the metronidazole at a stirring speed which is low but which makes possible a good dispersion of the active principle;
adding the appetizing substance (for example, chicken liver powder) at a stirring speed which is low but which makes possible a good dispersion of the appetizing substance.

In the case where the chosen viscosifying agent would result in a suspension, such as, for example, a silica, the preparation process might be carried out with a necessary rotor/stator and might comprise the following stages:

mixing, with stirring and heating, the oil (for example, Miglyol), the antioxidant (for example, BHT) and the surfactant;
adding the silica with stirring;
adding the metronidazole with stirring which makes possible a good dispersion of the active principle;
adding the appetizing substance (for example, chicken liver powder) with stirring which makes possible a good dispersion of the appetizing substance.

Here again, this is a specific example which a person skilled in the art will know how to adjust according to the geometry of the equipment and the ingredients used.

EXAMPLES

Example 1

The inventors first tested the acceptance of an oily metronidazole suspension alone; the aim of this study is to assess the spontaneous taking of metronidazole in the form of an oily suspension (liquid) presented alone in the bowls of animals.

The formulation tested has the following composition: 16.67% by weight/volume of metronidazole (with D50 at 67 µm and D90 at 154 µm, which means that 50% of the metronidazole particles have a diameter of less than 67 µm and that 90% of the metronidazole particles have a diameter of less than 154 µm) in Miglyol 812N, with 2% by weight/volume of aluminum monostearate or distearate, 4% by weight/volume of stearic acid, 5% by weight/volume of chicken liver powder and 0.02% by weight/volume of BHT, packaged in a brown glass bottle.

The tests on the taking of metronidazole were carried out on three dogs of the beagle breed having a mean weight of 10 kg; the metronidazole is presented for one hour to the dogs once daily for 6 days.

On each day of treatment, each animal received 3 ml/10 kg (the volume of product administered per animal remains the same throughout the duration of the study).

Out of the three animals tested, one tasted the suspension on the first two days, sniffed it on the following two days and ignored it on the final two days; the two other dogs consumed everything.

Conclusion: the oily metronidazole suspension according to the invention, administered to dogs for 6 consecutive days, presented alone in their bowls, was well appreciated by the majority of the animals.

Example 2

The aim of the study is to assess the taking of metronidazole in the liquid form over a defined amount of dry dog food.

The composition of each of the metronidazole suspensions tested is described in detail in the tables below, which also show the particle size characteristics of the metronidazole.

The tests on the taking of metronidazole were carried out on dogs of the beagle breed; these dogs, having a mean weight of 10 kg, receive 30 g of dry dog food to which the metronidazole suspension is added.

Various acceptance tests were carried out; each of these tests is carried out on 6 dogs by depositing a dose of suspension representing a contribution of 500 mg of metronidazole over 30 g of dry dog food; the compositions of the suspensions tested, the characteristics of the metronidazole used and the total consumption by the dogs are described in detail in the tables below.

The term "total taken" is understood to mean the amount of active principle taken by the dog (followed or not followed by swallowing) and the term "total consumption" is understood to mean the feed intake ingested (swallowed) by the dog.

It should be emphasized that the evaluation of the acceptance of the products tested is carried out under strict conditions since it is based on their total consumption.

Oily Suspensions Devoid of Appetizing Substance

The tests carried out with oily metronidazole suspensions at different particle sizes which do not comprise appetizing substance are summarized in table I:

TABLE I

| | | Metronidazole USP/EUR Ph | | | |
|---|---|---|---|---|---|
| | | 16.67 | 16.67 | 16.67 | 16.67 |
| Compositions of the oily suspensions tested | Particle size of the metronidazole particles | (sieved 90 μm) 90 μm max | D50: 67 μm D90: 154 μm | D50: 72 μm D90: 187 μm | D50: 98 μm D90: 223 μm |
| | Miglyol 812 N | 77.31 | 82.33 | 82.33 | 77.31 |
| | Aluminum monostearate | 2.00 | 1.00 | 1.00 | 2.00 |
| | Stearic acid | 4 | | | 4 |
| | BHT | 0.02 | | | 0.02 |
| Results | Total (%) | 100.00 | 100.00 | 100.00 | 100.00 |
| | % of total taken | 90 | 100 | 90 | 96.7 |
| | % of total consumption | 53.3 | 73.3 | 73.3 | 60 |

The results of table I show a good acceptance of the suspension devoid of appetizing substance when it is added to dry dog food; however, it is observed that the acceptance depends on the size of the metronidazole particles, the best results being obtained with a D90 of 154 μm and of 187 μm.

Oily Suspensions with Appetizing Substance, with or without Taste Enhancer

Similar tests carried out with oily metronidazole suspensions comprising an appetizing substance (chicken liver powder) are presented in table II:

TABLE IIa

| | | Metronidazole USP/EUR Ph | |
|---|---|---|---|
| | | 16.67 | 16.67 |
| Compositions of the oily suspensions tested | Particle size | D50: 2.8 μm D90: 6 μm | D50: 2.8 μm D90: 6 μm |
| | Miglyol 812 N | 76.33 | 77.33 |
| | Aluminum monostearate | 1.00 | 1.00 |
| | Stearic acid | | |
| | BHT | | |
| | Monosodium glutamate | 1.00 | |
| | Chicken liver powder | 5.00 | 5.00 |
| | Total (%) | 100.00 | 100.00 |

TABLE IIa-continued

| | | Metronidazole USP/EUR Ph | |
|---|---|---|---|
| | | 16.67 | 16.67 |
| Results | % of total taken | 90 | 90 |
| | % of total consumption | 40 | 43.3 |

TABLE IIb

| | | Metronidazole USP/EUR Ph | | | | | | |
|---|---|---|---|---|---|---|---|---|
| | | 16.67 | 16.67 | 16.67 | 16.67 | 17.84 | 16.67 | 16.67 |
| Compositions of the oily suspensions tested | Particle size | (sieved on 50 μm) | (sieved on 90 μm) | (sieved on 125 μm) | (sieved on 150 μm) | (sieved on 150 μm) | (sieved on 150 μm) | (sieved on 180 μm) |
| | Miglyol 812 N | 72.31 | 72.31 | 72.31 | 72.31 | 75.16 | 72.31 | 72.31 |
| | Aluminum monostearate | 2.00 | 2.00 | 2.00 | 2.00 | 1.00 | 2.00 | 2.00 |
| | Stearic acid | 4.00 | 4.00 | 4.00 | 4.00 | | 4.00 | 4.00 |
| | BHT | 0.02 | 0.02 | 0.02 | 0.02 | | 0.02 | 0.02 |
| | Monosodium glutamate | | | | | 1.00 | | |
| | Chicken liver powder | 5.00 | 5.00 | 5.00 | 5.00 | 5.00 | 5.00 | 5.00 |
| Results | Total (%) | 100.00 | 100.00 | 100.00 | 100.00 | 100.00 | 100.00 | 100.00 |
| | % of total taken | 96.7 | 96.7 | 96.7 | 100 | 96.7 | 96.7 | 90 |
| | % of total consumption | 56.7 | 56.7 | 50 | 60 | 83.3 | 60 | 56.7 |

Tables IIa and IIb show a good acceptance of the oily metronidazole suspensions, with the proviso that the latter are prepared with a specific particle size range of the metronidazole particles:

Oily Suspensions with Appetizing Substance at Different Metronidazole Contents

TABLE III

| | Metronidazole USP/EUR Ph | | | |
|---|---|---|---|---|
| | 16.67 | 12.5 | 10 | 8.33 |
| Particle size | D50: 67 μm D90: 154 μm | D50: 67 μm D90: 154 μm | D50: 67 μm D90: 154 μm | D50: 67 μm D90: 154 μm |
| Miglyol 812 N | 77.33 | 81.50 | 84.00 | 85.67 |
| Aluminum monostearate | 1.00 | 1.00 | 1.00 | 1.00 |
| Chicken liver powder | 5.00 | 5.00 | 5.00 | 5.00 |
| Total (%) | 100.00 | 100.00 | 100.00 | 100.00 |
| % of total taken | 93.3 | 96.7 | 100 | 96.7 |
| % of total consumption | 80 | 80 | 90 | 93.3 |

These results show that the metronidazole content has an influence on the total consumption of the suspension; however, this consumption remains highly satisfactory under the conditions tested.

These combined tests carried out confirm the excellent acceptance of the oily metronidazole suspensions according to the invention.

The invention claimed is:

1. A method for improving the acceptance by a domestic animal of an oral treatment for inflammatory diseases of the intestines, the method comprising administering to the domestic animal an effective amount of an oily metronidazole suspension comprising:
    a) between 5% and 30% by weight/volume of metronidazole;
    b) between 70% and 95% by weight/volume of at least one edible animal, vegetable or mineral oil; and
    wherein the metronidazole is provided in the form of particles of metronidazole, at least 90% of which have an equivalent diameter strictly between 50 and 250 μm and wherein said particles are devoid of coating.

2. The method of claim 1, wherein the method improves observance of the treatment by the domestic animal.

3. The method of claim 1, wherein the suspension further comprises
    a) between 0.1% and 5% by weight/volume of a viscosifying agent chosen from aluminum mono-, di- or tristearate, hydrophilic colloidal silica or hydrogenated castor oil; and/or
    b) between 0.1% and 5% by weight/volume of at least one nonionic surface-active principle chosen from stearic acid and polysorbate 80.

4. The method of claim 1, wherein the suspension further comprises between 0.1% and 5% by weight/volume of aluminum monostearate or aluminium distearate.

5. The method of claim 1, wherein the oil of the suspension is chosen from soybean oil, coconut oil, palm oil, esters derived from fatty acid, coupled with glycerol or propylene glycol, cod liver oil, paraffin oil or their mixture.

6. The method of claim 1, wherein the suspension further comprises between 0.1% and 0.5% by weight/volume of at least one antioxidant chosen from butylated hydroxyanisole (BHA), butylated hydroxytoluene (BHT), propyl gallate, ascorbyl palmitate, α-tocopherol or their mixture.

7. The method of claim 1, wherein the suspension is administered at a dose representing a contribution of metronidazole of between 10 and 50 mg/kg of body weight twice daily.

8. The method of claim 1, wherein at least 90% of the metronidazole particles have an equivalent diameter of strictly between 125 and 200 μm.

9. A method for improving the acceptance by domestic animals of an oral treatment for diarrhea, the method comprising administering to the domestic animal an effective amount of an oily metronidazole suspension comprising:
    a) between 5% and 30% by weight/volume of metronidazole;
    b) between 70% and 95% by weight/volume of at least one edible animal, vegetable or mineral oil; and
    wherein the metronidazole is provided in the form of particles of metronidazole, at least 90% of which have an equivalent diameter strictly between 50 and 250 μm and wherein said particles are devoid of coating.

10. The method of claim 9, wherein the method improves observance of the treatment by the domestic animal.

11. The method of claim 9, wherein at least 90% of the metronidazole particles have an equivalent diameter of strictly between 125 and 200 μm.

12. The method of claim 9, wherein the suspension further comprises
    a) between 0.1% and 5% by weight/volume of a viscosifying agent chosen from aluminum mono-, di- or tristearate, hydrophilic colloidal silica or hydrogenated castor oil; and/or
    b) between 0.1% and 5% by weight/volume of at least one nonionic surface-active principle chosen from stearic acid and polysorbate 80.

13. The method of claim 9, wherein the suspension further comprises between 0.1% and 5% by weight/volume of aluminum monostearate or aluminium distearate.

14. The method of claim 9, wherein the oil of the suspension is chosen from soybean oil, coconut oil, palm oil, esters derived from fatty acid, coupled with glycerol or propylene glycol, cod liver oil, paraffin oil or their mixture.

15. The method of claim 9, wherein the suspension further comprises between 0.1% and 0.5% by weight/volume of at least one antioxidant chosen from butylated hydroxyanisole (BHA), butylated hydroxytoluene (BHT), propyl gallate, ascorbyl palmitate, α-tocopherol or their mixture.

16. The method of claim 9, wherein the suspension is administered at a dose representing a contribution of metronidazole of between 10 and 50 mg/kg of body weight twice daily.

17. The method of claim 9, wherein the diarrhea is of parasitic origin.

18. The method of claim 9, wherein the diarrhea is giardiasis.

* * * * *